May 28, 1935. E. W. HARTMAN Plant Pat. 125

APPLE

Filed Dec. 22, 1933

INVENTOR
E. W. HARTMAN

By Mason Fenwick & Lawrence
ATTORNEYS

Patented May 28, 1935

Plant Pat. 125

UNITED STATES PATENT OFFICE

125

APPLE

Edgar W. Hartman, Cashtown, Pa., assignor, by direct and mesne assignments, of one-fourth to Buntings' Nurseries, Selbyville, Del., a corporation of Delaware, one-fourth to Waynesboro Nurseries, Inc., Waynesboro, Va., a corporation of Virginia, and one-fourth to Harrisons' Nurseries, Inc., Berlin, Md.

Application December 22, 1933, Serial No. 703,620

1 Claim. (Cl. 47—62)

This invention relates to a new and distinct variety of apple.

It is a sport of the York Imperial, with which it is substantially identical in size, shape, flavor and keeping qualities, but differing therefrom in color and in being somewhat earlier in maturing.

Figure 1:
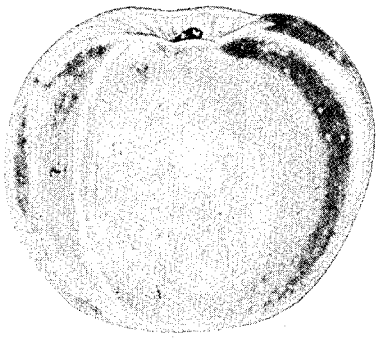
Figure 2:
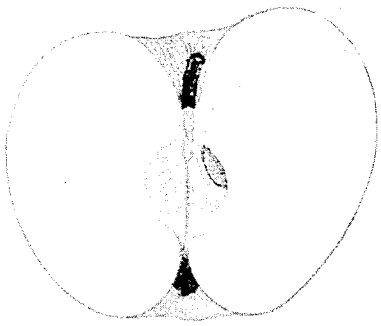

The apple of the present invention is disclosed in the accompanying water color reproduction from an actual specimen, in which Figure 1 is a view of the apple in perspective, Figure 2 being an axial section.

In contrasting the new apple of the present invention with a York Imperial of the normal type, there are no distinguishing differences in the color or texture of the flesh or in its flavor. Externally considered, the appreciable distinction relates to the color of the skin. The new apples are notably uniform in color and as uniform in size and shape as can be expected in a normally developed York Imperial tree. The characteristic shape of the apple is roundish truncate, the truncate character being well developed. In comparison with the normal York Imperial apple, the apple of the present invention has a much greater wash or over-spread of red which practically covers the entire surface to the extent that it is impracticable to make any color reading of the under color. The shade of red in a normal York Imperial apple and which covers only part of the surface compares with shades 9L and 10L on plate 4 in Maerz and Paul's dictionary of color. The green on the normal York is found to fall between shades 3 and 4 of plate 1 in Department of Agriculture Bulletin No. 1448. The shade of red in the new apple falls between shades 6L and 7L, plate 5 of Maerz and Paul's dictionary, shade 7L tending perceptibly toward a purplish cast. The purplish cast of the new apple is more pronounced than the purplish cast of the normal apple. The same over-spread of gray which characterizes the normal York Imperial apple also appears on the new sport. There is practically no green perceptible on the sport. There are no varietal distinctions between the normal York Imperial and the new apple as regards the dots.

The new variety is particularly valuable in view of its color, enhancing the appearance of the pack when mixed with York Imperials or when used as a topping layer for the latter. On account of its somewhat earlier maturity, it may be brought to market from ten days to three weeks earlier than York Imperials, its decided coloration also favoring earlier marketing.

The new apple was discovered on a single limb of a mature tree of York Imperial, in the orchard of E. W. Hartman at Cashtown, Pennsylvania, every apple on the said limb being of the new variety. The new apple was propagated by grafts taken from said limb and grafted upon French apple seedlings. There are at the present time, about five hundred young apple trees in existence, eventuating from these grafts, all of which are true to the new variety.

What I claim is:

The apple as described and shown, being a sport of York Imperial having substantially the same characteristics of size, shape, flavor and keeping qualities as the York Imperial, but distinguishing therefrom in color which is a deep purplish carmine almost uniformly covering the surface of the apple and showing pale or russet dots distributed over the surface of the apple with fair uniformity.

EDGAR W. HARTMAN.